United States Patent [19]

Piasio et al.

[11] 4,225,575
[45] Sep. 30, 1980

[54] METHOD AND APPARATUS FOR PERFORMING IN VITRO CLINICAL DIAGNOSTIC TESTS USING A SOLID PHASE ASSAY SYSTEM

[75] Inventors: Roger N. Piasio, Yarmouth; David A. Perry, Portland, both of Me.; Pangal N. Nayak, Belmont, Mass.

[73] Assignee: Ventrex Laboratories, Inc., Portland, Me.

[21] Appl. No.: 905,552

[22] Filed: May 15, 1978

Related U.S. Application Data

[63] Continuation-in-part of Ser. No. 805,480, Jun. 10, 1977, abandoned.

[51] Int. Cl.² .............. G01N 33/16; A61K 43/00; B01J 1/22
[52] U.S. Cl. .................. 424/1; 23/230 B; 422/57; 422/58; 424/12; 435/6
[58] Field of Search .......... 424/1, 12; 206/206, 206/569; 23/253, 259, 230 B; 195/103.5 A; 422/57, 58

[56] References Cited

U.S. PATENT DOCUMENTS

| | | | |
|---|---|---|---|
| 3,206,602 | 9/1965 | Eberle | 424/1 |
| 3,464,798 | 9/1969 | Kilthau | 23/253 |
| 3,652,761 | 3/1972 | Weetall | 424/1 |
| 3,826,619 | 7/1974 | Bratu, Jr. et al. | 424/1 |
| 3,867,517 | 2/1975 | Ling | 424/1 |
| 3,918,909 | 11/1975 | Aruman | 23/253 R |
| 3,932,141 | 1/1976 | Beall et al. | 424/1 |
| 3,935,074 | 1/1976 | Rebenstein et al. | 424/1 |
| 4,048,298 | 9/1977 | Niswender | 424/1.5 |
| 4,111,754 | 9/1978 | Park | 195/103.5 R |
| 4,116,638 | 9/1978 | Kenoff | 23/230 B |

OTHER PUBLICATIONS

Felgner, P., Zbl. Bakt. Hyg., I. Abt. Orig. A., 240, (1978), pp. 112, 118.

Primary Examiner—Benjamin R. Padgett
Assistant Examiner—Christine M. Nucker
Attorney, Agent, or Firm—Irons and Sears

[57] ABSTRACT

A method and apparatus for conducting chemical reactions at a liquid-solid interface wherein a reaction component is fixed on the surface of a solid phase immersed in a liquid phase containing a freely diffusing, mobile reaction component. The apparatus comprises a substantially smooth-surfaced matrix of appropriate geometrical configuration designed to provide a large surface to volume ratio, a short transfer distance from the mobile component to the fixed component distributed on the solid phase surface and to drain freely upon removal from the reaction liquid.

40 Claims, 15 Drawing Figures

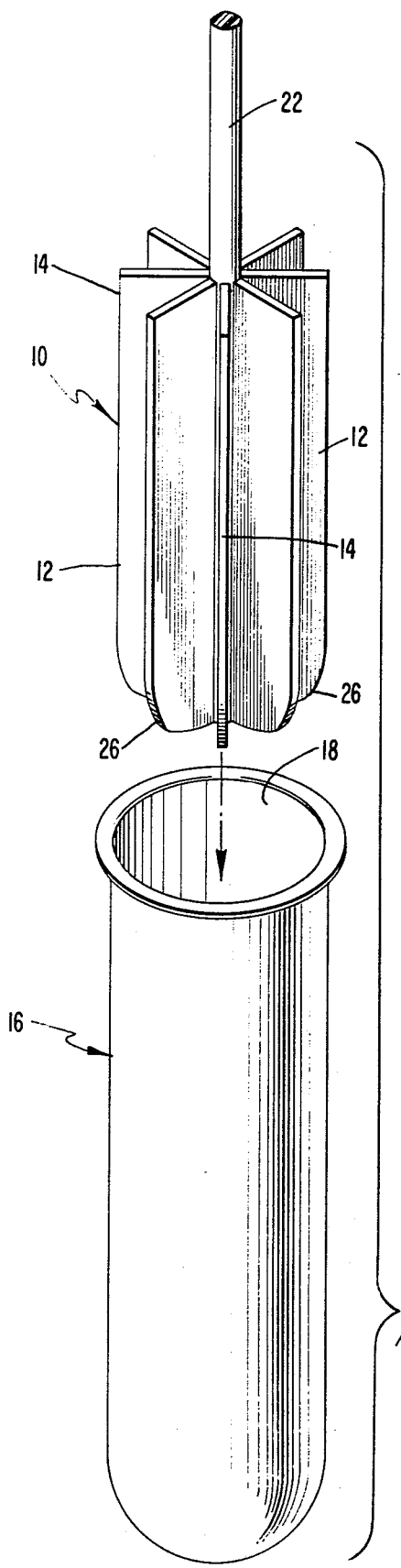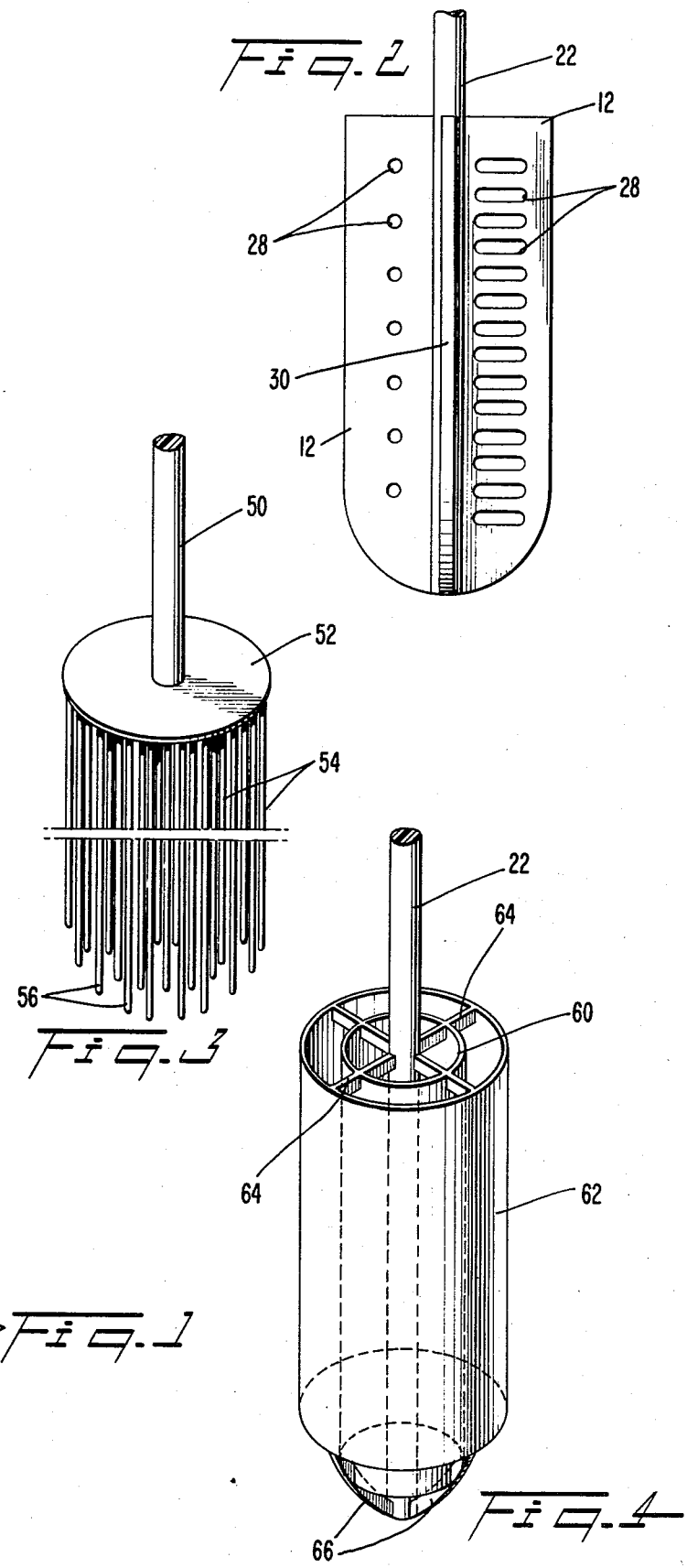

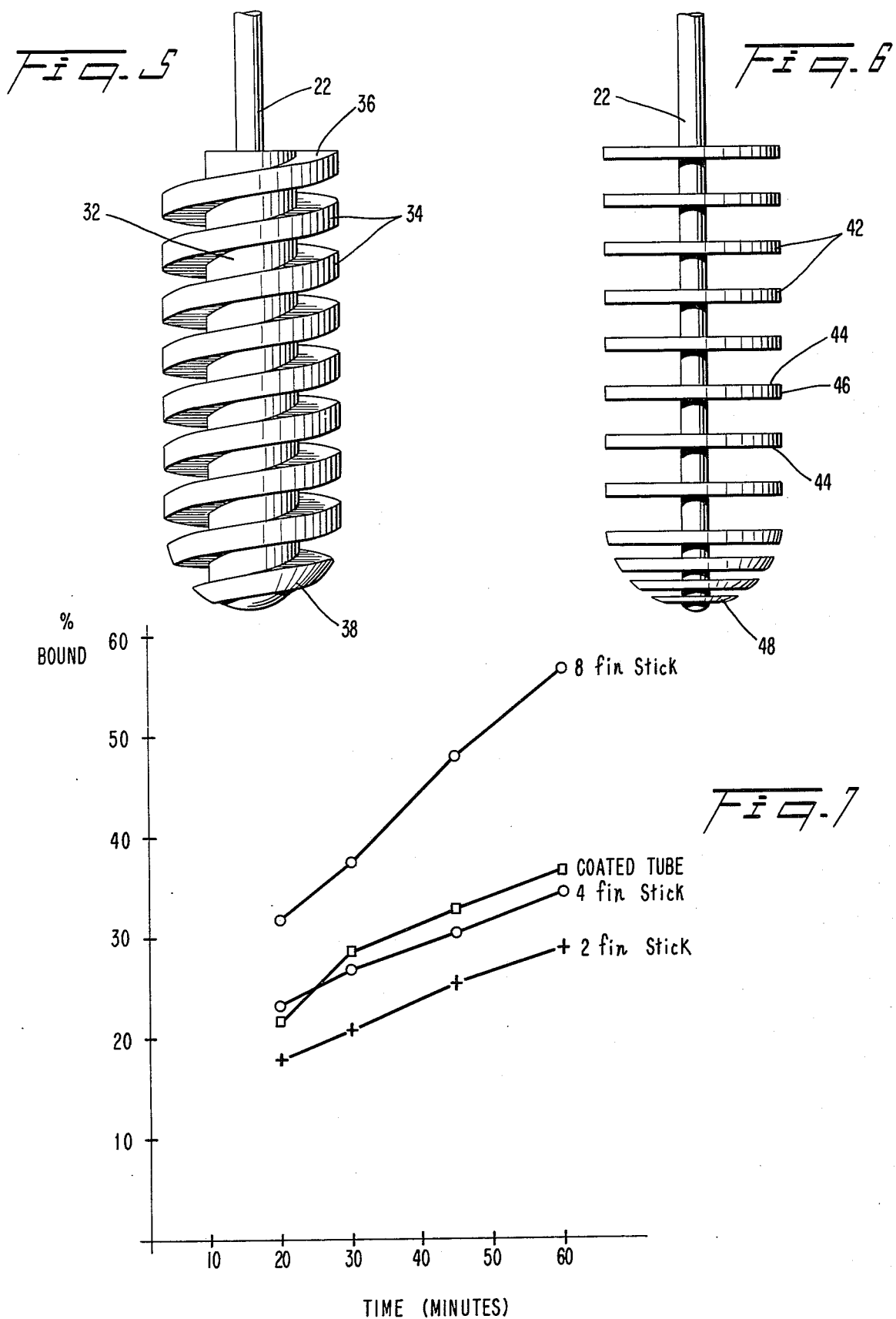

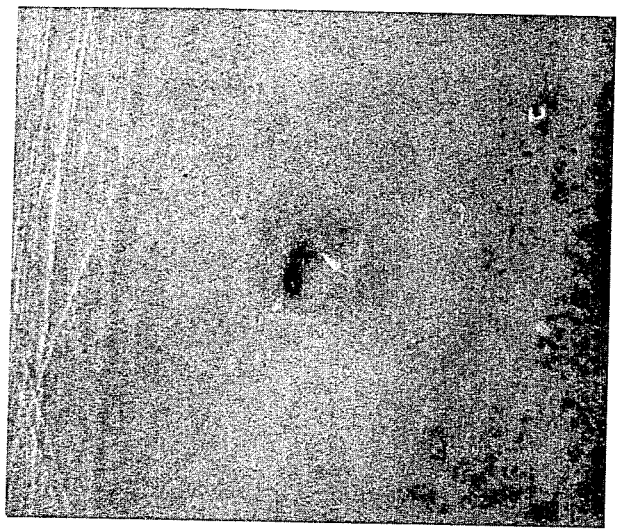
Fig. 14-a
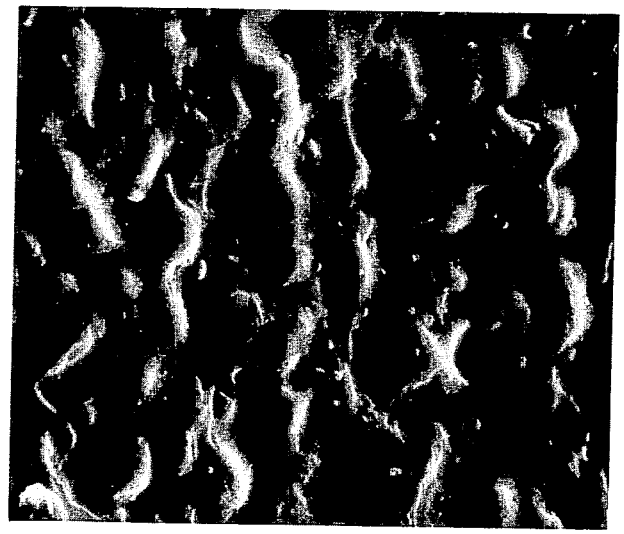
Fig. 14-b

METHOD AND APPARATUS FOR PERFORMING IN VITRO CLINICAL DIAGNOSTIC TESTS USING A SOLID PHASE ASSAY SYSTEM

This application is a continuation-in-part of copending application Ser. No. 805,480, filed June 10, 1977, abandoned.

BACKGROUND OF THE INVENTION

In recent years, numerous techniques have been employed in the area of laboratory diagnostics to simplify operating procedures of existing methods and to provide new methods of improved speed, sensitivity, and accuracy. In particular, solid phase reactions have been especially valuable in simplifying the manipulations of prior art procedures and making possible procedures that could not be performed with conventional homogeneous phase reactions.

A solid phase reaction is generally carried out between one reactant, the fixed component, immobilized on the surface of an insoluble support matrix, and a second reactant, the mobile component, in solution. The reaction occurs when a molecule or a molecular arrangement of the mobile reactant, in the course of diffusion, collides with a molecule of the fixed reactant immobilized on the surface of the solid support matrix. The reaction may be a conventional chemical reaction, a binding of the mobile component by the fixed component as in an immunochemical reaction between an antigen and an antibody, or it may be a binding of the mobile component by the fixed component accompanied by chemical transformation of one of the components such as occurs in an enzyme-catalyzed reaction. Quantitative results are obtained by measuring the formation of products or disappearance of reactants as in the case of conventional and enzyme-catalyzed reactions, and in measuring the amount of the mobile component bound or the amount of mobile component unbound, in the case of an immunochemical reaction.

Any conventional chemical reaction or enzyme-catalyzed reaction resulting in a directly or indirectly measurable change can, in principle, be carried out by solid phase techniques. Directly measurable changes include changes in pH, light absorbance in the visible and ultraviolet regions or changes in fluorescence intensity. Indirect measurements can be made whenever the primary reactants or products are not readily measurable themselves by interposing the action of a reagent to carry out further reaction steps resulting in a measurable change and by the introduction of specific separation techniques. Such strategies may be employed alone or in combination, as is understood in the art.

Where the reaction consists solely of binding, in the absence of chemical change, techniques developed in the field of immunochemistry may be used to measure the extent of the reaction. Solid phase reactions are especially suited for immunochemical assays because the reactants in bound form may readily be removed from the solution by virtue of their attachment to the solid phase. Frequently, however, the components bound in an immunochemical reaction cannot be directly measured because they are indistinguishable by chemical methods from other substances commonly present in the same reaction mixture, so that the mere disappearance of a reactive component from solution or its accumulation on the solid phase cannot be measured directly. Therefore, additional steps must be taken in order to make a measurable change related to the amount of binding.

The variety of approaches taken by workers in the prior art can be grouped into two general categories. In the first of these, termed competitive or indirect immunoassays, the immobilized component is present in controlled amount and the mobile component present in unknown amount. To the unknown amount of mobile component is added a known amount of the same component which has been tagged by the addition of a measurable substituent which does not interfere with its immunochemical reactive properties. The tag may consist of a radioisotope, a chromophore, a fluorophor or an enzyme. The amount of tagged material bound immunochemically to the solid phase will depend upon the amount of untagged component in solution competing for the same binding sites. The more of the unknown present, the less will be the amount of tagged component bound.

In the second general method, termed the sandwich method or direct method, the solid phase containing an amount of immunochemically bound mobile component resulting from the first immunochemical reaction is subjected to the action of a reagent which can also bind immunochemically to the solid phase, but only at sites already occupied by the immunochemically bound mobile component. The reagent may be tagged, for example, as in the first method with a radioisotope, a fluorophor, a chromaphore or an enzyme. The amount of tagged reagent bound is a direct measure of the amount of mobile component bound, which, in turn, is a measure of the amount of mobile component initially present in the reaction mixture.

Where the tag is a radioisotope, the technique, whether competitive or noncompetitive, is termed a radioimmunoassay. When the tag is an enzyme, the assay is termed an enzyme-linked immunoassay. The amount of enzyme-tagged reactant is measured by any convenient method for measuring the activity of the enzyme used in the tag.

Other kinds of solid phase reactions of the type generally described hereinabove are presented by way of example. The immunoradiometric assay for quantitative determination of an antigen is conducted by first reacting a known excess of labeled antibody with the unknown amount of antigen in a homogeneous phase reaction. Subsequently, immobilized antigen in excess amount is added in order to bind the unreacted soluble labeled antibody. The amount of unknown antigen is determined by measuring the difference between the total labeled antibody and the amount bound to the solid phase. The method gives direct quantitative results only with an univalent antigen, i.e., antigen which can only bind one molecule of antibody.

Enzyme-catalyzed reactions are conveniently carried out in solid phase systems. An enzyme immobilized on a solid phase matrix may be used to quantitatively assay for, or qualitatively detect the presence of, the substrate for the enzyme in a sample of biological material. For example, lactic acid in serum may be measured using a matrix coated with lactic dehydrogenase. Similarly, urea may be assayed using a solid phase insert bearing immobilized urease. In addition to clinical applications, enzyme assays may be used for quality control monitoring of industrial process steps and also for carrying out process steps. As an example of the former, immobilized penicillinase could be employed in an assay to monitor the quality of penicillin produced during the process of manufacturing the drug. As an example of the latter, immobilized proteases or nucleases could be useful to remove or inactivate contaminating proteins or nucleic acids. The inserts of the present invention may be conveniently removed at any desired stage of the reaction so that the extent of the desired reaction could be controlled readily.

The presence of an enzyme of clinical significance in a sample of biological material may also be assayed by providing a substrate for the enzyme immobilized on a solid phase matrix. An example of an assay which could be adapted for use in this fashion is the method disclosed in U.S. patent application No. 795,497 of James W. Ryan and Alfred Chung. A Lysozyme assay, in which radioactively labeled *Micrococcus lysodeikticus* is covalently bound to the surface of a solid phase matrix, further exemplifies the use of an immobilized substrate in an enzyme assay reaction.

Further examples of useful solid phase reactions are provided for by the specific binding reactions of certain proteins. These include, for example, β-lactoglobulin, which specifically binds folic acid, specific receptor proteins capable of binding hormones, such as the receptor substance purified from rat mammary tumor cells which specifically binds prolactin and the variety of plant proteins such as concanavalin A, which are capable of specifically binding certain carbohydrates.

Conventional chemical reactants may be designed for use in solid phase reactions. Solid phase reactants capable of forming colored complexes, as by the formation of glycosyl derivatives or by diazo coupling to a reagent immobilized on the surface of a solid phase matrix could be devised for use, either alone or in combination with an enzyme-catalyzed reaction, to provide for a color change on the surface of the matrix. Also, ion-exchange reactions may conveniently be conducted using a solid phase matrix of the present invention. The foregoing examples are illustrative only and additional possibilities will be apparent to those having ordinary skill in the appropriate art.

In such solid phase technology, the reagent or reagents used in the procedure are usually immobilized by being coated or bonded, either covalently or by adsorption to the solid phase material, which is then immersed in the sample to be tested. The manner of coupling such reagents to the solid phase material is known. See, for example, the disclosures in U.S. Pat. Nos. 3,652,761, 3,879,262 and 3,896,217.

Examples of commonly used solid phase materials include, but are not limited to, glass or polymeric tubes which are coated with the reagent or reagents on their internal surfaces; polymeric coated sticks; micro and macro beads formed of polymers and of glass and porous matrices.

Immunochemical assays are highly useful in clinical research and diagnosis. They are highly specific, owing to the highly selective nature of antigen-antibody reactions. The antigen-antibody binding is very tight so that once the binding reaction has had an opportunity to occur, the limit of detectability is determined by the measurability with which the tag can be detected. Immunochemical assays are exceedingly versatile, owing to the fact that they can be used to measure specific substances selectively against a background of chemically similar substances. Because of these desirable attributes, there has been considerable interest in improving the ease of manipulation, sensitivity, accuracy, speed and applicability of immunochemical assays. The development of solid phase immunoassays has been one of the major advances in the field.

Among the advantages of solid phase systems is that the reaction product or products can be separated from the reaction solution with relative ease, i.e., by physically removing the solid phase material. This is in contrast with a non-solid phase or a homogeneous reaction, which typically results in a homogeneous solution which requires more complex separation techniques.

The introduction of solid phase technology has permitted the performance of novel procedures that were heretofore extremely difficult using free solution technology. An example of this is the sandwich assay technique described hereinabove. To be carried out in homogeneous solution, the sandwich technique would require a large excess of one of the reactants. More importantly, separation of the first antigen-antibody complex from a homogeneous phase solution requires the use of sophisticated physical-chemical techniques, especially if the antigen is relatively small compared to the antibody and molecular weight differences between free antibody and complexed antibody are slight. In contrast, the separation procedure in a solid phase system is a matter of the utmost simplicity. As will be described below, one of the primary advantages of solid phase technology, the ease of separating the solid and liquid phases, is maximized in the practice of the present invention, which provides extremely simple means for separating the phases.

While, in theory, solid phase technology offers numerous advantages over free solution or homogeneous systems, it does have certain limitations due principally to the solid phase configurations heretofore used. For example, since at least one of the reactants in a solid phase system is effectively immobilized by being bound to the surface, the reaction rate of solid phase systems is generally slower than that of homogeneous or free solution systems. Additionally, there is normally a maximum amount of reagent which can be bound to the solid phase surface, the maximum amount being generally dependent upon the surface area, the purity of the reagent and the specific procedure used to bind the reagent to the surface. Optimally, as much as possible of the surface area of the solid material should be coated so as to increase the reaction rate and decrease the reaction time.

The earliest solid phase systems devised were test tubes coated on the inside surface. Commerical examples of coated tube technology include the Immunotube TM system marketed by Smith Kline Instruments of Sunnyvale, California, and the Rianen TM system of New England Nuclear, North Billerica, Mass., and the tubes described in U.S. Pat. No. 3,867,517 issued Feb. 18, 1975 to Ling. Although coated tube systems have proven useful for immunoassay purposes, they fail to exploit the full range of potential advantages offered by solid phase systems. A principal disadvantage is that the surface to volume ratio is relatively low and reaction kinetics may be further hindered by the fact that the reactive surface is located at the boundary of the solution volume, which may be relatively remote from the main body of the solution. Therefore, the average distance between mobile reactants and the reactive surface is large. In addition, each test tube must be coated separately under static conditions and this constraint is likely to result in variations from tube to tube in the amount of coating material applied and ultimately in the assay results. The coating that is produced may be nonuniform or even discontinuous, such that some areas of potentially reactive surface are devoid of coating while others may be too heavily coated for optimal reactivity. In either case, the amount of surface actually available for reaction with the mobile component is reduced, in a non-uniform way, with corresponding loss of sensitivity and reproducibility. The batchwise method of coating tubes is also relatively expensive. Reactions conducted in coated tubes are subject to errors caused by convection in the reaction fluid. Results varying as much as 10-fold can be caused by convection in these systems.

Attempts to improve on the performance of coated tubes have led to a variety of systems designed to increase the surface to volume ratio of the solid phase system. These methods have included providing highly convoluted surfaces, reducing the volume of liquid required and providing surfaces of finely divided material.

The SPAC TM system of Mallinkrodt Chemical Company is basically a coated tube system which exemplifies the strategy of providing a convoluted surface to increase surface area in the coated tube format. Additionally, the tubes are provided with a detachable lower section which may be batch coated to achieve greater uniformity from tube to tube. A consequence of the batch immobilization on coated tube bottoms is that the outside as well as the insides of the tubes become coated. This makes it difficult for the laboratory technician to work with the tubes without coming into contact with whatever material is coated on their surface and valuable immunological reactants are wasted. The convoluted surface area is said to increase by 3-4 times the amount of reactive surface available. However, the reactive surface remains at the periphery of the solution, which may be suboptimal geometry from the standpoint of the average diffusion distance from the solution to the reactive surface. Due to the complexity of the surface, difficulties in washing the surface free of contaminating substances may be encountered. As with coated tube systems in general, the SPAC TM system is likely to be sensitive to convection currents which can result in large errors as previously described. Convection may be reduced by carrying out the reaction in a constant temperature bath. However, this procedure presents additional equipment requirements for the clinical laboratory. For measurement of hapten antigens, the system is additionally suboptimal if the reaction is carried out at 37° C. according to the manufacturer's recommendation. It has been shown that increasing the temperature of certain antibody-hapten reactions tends to enhance the rate of dissociation of the antibody-hapten complex relative to the rate of its formation. See Smith, T. W., and Skubitz, K. M., *Biochemistry* 14, 1496 (1975) and Keave, P. M., Walker, W. H. C. Gauldie, J. and Abraham, G. E., *Clin. Chem.* 22, 70 (1976).

Various types of solid phase matrices designed to be inserted into the reaction fluid have been disclosed. A convoluted or sponge-like matrix designed to be inserted into the test solution is exemplified by U.S. Pat. No. 3,951,748, issued Apr. 20, 1976 to Devlin. This material offers relatively large surface areas but may be difficult to wash or drain thoroughly at the conclusion of the reaction. In addition, such systems may be limited in practice to the use of reactants and reagents which are readily eluted from the sponge matrix. More significantly, the sponge matrices tend to react extensively with only a portion of the reaction fluid, i.e., that portion which actually penetrates the pores of the matrix.

A second type of insert, employing the strategy of forcing the reaction fluid to spread in a thin layer over the coated matrix surface, is disclosed in U.S. Pat. No. 3,826,619, issued July 30, 1974 to Bratu, et al., and U.S. Pat. No. 3,464,798, issued Sept. 2, 1969, to Kilthau. Both cases disclose a combination of a receptacle and a closely-fitting insert matrix, so shaped as to squeeze the reaction fluid into a thin layer between the container walls and the matrix surface. The insert matrix must fit the container with a close tolerance, and the volume of reaction fluid must be carefully controlled, since variations could adversely affect the reproducibility of the assay. The apparatus of Bratu is designed for use in a direct immunochemical test that is qualitative only. Because the reaction solution is forced into a thin film by the insert, the reaction volume must necessarily be small and Bratu in fact discloses that the type of assay contemplated is designed for small volumes of undiluted serum. One of the pitfalls in this type of assay is that errors in the rates of antigen-antibody reactions may be caused by variations in the pH of undiluted serum, which may vary between pH 6 and pH 9 in clinical samples. The pH may be controlled by the addition of buffer, but buffer salt concentrations greater than 0.1 M tend to dissociate antigen-antibody complexes. Therefore, an excess volume of low ionic strength buffer must be used to control pH accurately, and this may expand the reaction volume to an unacceptable amount. Error due to pH may be tolerated in a qualitative assay such as disclosed by Bratu, et al., especially in samples relatively rich in concentration of unknown, but not in the quantitative assays for which the present invention is designed. Where diluting by buffer is required, a low concentration of unknown may be diluted below the level of detection, leading to false negative results with the Bratu or Kilthau device. One embodiment of the Bratu insert is a finned insert somewhat similar in appearance to the 4-fin stick embodiment of the present invention. Its use is disclosed for qualitative analysis where larger quantities of serum are available but there is no suggestion of any different mode of operation from the thin film mode utilized with the rounded or conical version. The devices disclosed in U.S. Pat. No. 3,826,619 have not, so far as is known, been commercially exploited.

A third type of solid phase insert matrix is represented by the StiQ TM assay of International Diagnostic Technology Corporation, Santa Clara, Calif., designed to exploit a solid phase assay disclosed in U.S. Pat. No. 4,020,151, issued Apr. 26, 1977 to Bolz, et al. In this system, a disc shaped, uncoated insert matrix of material capable of adsorbing proteins from serum is provided. In this system, the limitations are not only due to surface to volume ratio or geometric considerations but are mainly due to problems associated with the initial adsorption step, such as the presence of interfering substances and the difficulty of obtaining measurable adsorption components present in low concentration.

Another example of an attempt to improve surface to volume ratio by reducing reaction volume is disclosed by Friedel, R. and Dwenger, A., *Clin. Chem.* 21, 967 (1975). In this system, capillary tubes are coated on the inside with a specific adsorbant and the reaction mixture is introduced into the lumen of the capillary tube.

One system which affords a high surface area for over-all volume is the coated micro glass bead system as, for example, the Immo Phase TM system of Corning Glass Works. This system exemplifies the use of finely divided particles. It provides a high coated surface area with a correspondingly high reaction rate. Due to settling of the particles during the reaction, optimization of test systems of this kind require that the test tubes in which they are placed during reaction be capped and mixed vertically during reaction to insure that all surfaces come in contact with the reactants. Further, the use of particles necessitates multiple centrifugations and washings to completely separate the immobilized product from the solution reactants. Glass particle surfaces have the further disadvantage that there is greater non-specific protein binding to glass, as compared to plastic.

Prior attempts to improve on coated tubes as a solid state reaction matrix have generally resulted in some improvement in reaction rate, or the time necessary to carry out a measurable reaction. Such improvement has generally been accomplished by a concomitant increase in manipulative difficulty, or loss of flexibility. The present invention provides both improved surface to volume ratio and improved reaction kinetics, while providing improved versatility and ease of manipulation.

Another possibly pertinent patent, though not employing a solid phase matrix, is U.S. Pat. No. 3,206,602 issued Sept. 14, 1965 to Eberle.

SUMMARY OF THE INVENTION

The present invention provides a method for conducting a chemical, enzymatic or immunochemical reaction wherein one or more of the reactants, each termed a fixed component, is affixed to a solid phase surface and one or more other reactants, each termed a mobile component, is freely diffusible in a liquid medium in which the solid phase is immersed. In particular, a fixed reactant is attached to a unitary matrix which may be immersed in the liquid. The shape of the matrix is so constructed as to provide a large surface to volume ratio for the reaction, to provide a short transfer distance for the mobile reactants from the solution to the solid phase surface and to drain freely upon removal from the reaction liquid.

Advantages of the invention include the elimination of timing errors in starting and stopping reactions, high reaction rates, reduction of volumetric transfer errors, reduced error of measurement at a given level of sensitivity and ease of manipulation. The high reaction rate with the preferred embodiments permits immunochemical assays to be conducted at room temperature or lower, which may be advantageous over higher temperatures for reactions that approach equilibrium. The device is expected to provide ease of manufacture with consequent economy and uniformity of product. It may readily be appreciated that a wide variety of matrices may be designed, according to the principles and teachings disclosed herein. The essential features of the matrix include a handle member and a plurality of essentially smooth plane or curved surfaces attached thereto, so arranged, shaped and sized with respect to the reaction fluid that insertion of the matrix therein reduces the average diffusion distance of mobile component molecules to the matrix surfaces compared to their average diffusion distance to the reaction vessel inner surfaces when no matrix is present. The specific embodiments described and depicted herein are exemplary only, and not intended to limit the range of possible devices that could be constructed according to the invention. The actual shape of a given matrix of the present invention may, but need not be designed according to the size and shape of the reaction vessel into which it is to be placed. Moreover, as will be readily appreciated, there is no requirement for a close tolerance or snug fit within the reaction vessel. Further, it will be appreciated that the matrix must extend substantially throughout the depth of the fluid sample. In some systems, the matrix surfaces preferably extend above the surface of the reaction fluid, thereby producing an essentially constant geometric relationship throughout the depth of the reaction fluid and further providing that the same geometric relationship will occur, regardless of any changes in the fluid volume. Devices of the preferred embodiment of a given size, for example, are equally suited to assays where the reaction volumes differ by as much as 3-fold.

The use of the preferred fin-stick geometry has resulted, in some instances, in an unexpected and presently unexplained enhancement of reaction rate over that predicted on the basis of surface area. Because of the discovery that geometrical factors affect reaction rate, it has become important to provide uniform solid phase geometry from one sample to the next, in order to achieve uniform results. The devices of the present invention provide such uniformity, and further help to eliminate human and mechanical errors such as variations in agitation rate, timing errors, convection and the like.

DETAILED DESCRIPTION

In the process of the present invention, a solid phase reaction is carried out using one or more of the reaction components fixed to the surface of a matrix inserted into the reaction fluid. For purposes of illustration, reactions carried out in test tubes are described and matrices designed to be inserted into test tubes are discussed. The reaction is readily initiated by placing the matrix into the tube containing the mobile component and may be terminated by removing the insert. If desired, the reaction may be re-initiated simply by reinserting the matrix, or a second reaction initiated by inserting a new matrix bearing a second fixed component. The matrix may be placed in a second tube containing a reagent, if desired, or transferred directly to a radioactivity counting chamber or other measurement device, depending upon the nature of the assay method.

The solid phase reaction kinetics are more complex than for homogeneous phase reactions. A detailed theoretical basis for optimizing insert design is not available. However, certain basic considerations of a general nature can be taken into account. The total surface area in contact with the solution is an important factor. The larger the area, the greater the amount of fixed component which may be present in the reaction. Increasing the effective concentration of either component will generally increase the overall reaction rate. Since the amount of the fixed component is determined by, among other factors, the area of the solid phase, the reaction rate should vary directly with the surface to volume ratio. An increased surface to volume ratio is achieved in the present invention by providing an insert which has an increased surface area relative to that available on the inner surface of the test tube. A second factor possibly affecting reaction rate is the average diffusion distance between the mobile and fixed reactants. As is evident, "average diffusion distance" means the sum of the distances each of the mobile component molecules must diffuse, by the shortest possible path to reach a fixed component, divided by the total number of such molecules. The matrices of the present invention are designed to greatly reduce the average diffusion distance of mobile phase molecules to a fixed component adhering to the surface elements of the matrix relative to the average diffusion distance of such molecules to a fixed component held on the inner surfaces of the reaction vessel when no matrix is present. Transfer of mobile reactants to the reactive surface is thought to be facilitated by decreasing the average distance between mobile reactants and the reactive surfaces. Increased reaction rates have been observed using the inserts of the present invention, as described in detail in the examples.

Unexpectedly, it was observed in a number of cases that the observed increase in reaction rate was greater than expected on the basis of the increased surface-volume ratio. Similarly, reactions appeared to approach equilibrium sooner with the use of finned stick matrices than with the use of a coated tube. Although these phenomena are not well characterized or quantified, they appear to be more frequently observed and more readily apparent with the use of finned sticks having a greater number of fins.

While not consistently observed, the phenomena of enhanced reaction rate and more rapid approach to equilibrium occur with sufficient frequency to warrant the suggestion that geometrical factors of matrix configuration other than surface area per se can significantly affect solid phase reaction rates. Therefore, the use of matrices of the present invention is expected to provide advantageous reaction rates for solid phase reactions in general. It will be readily recognized that practical considerations are likey to dictate an upper limit of separate elements such as fins that may be affixed to the handle of the stick. For example, the elements should not be too closely spaced, or else capillary forces will cause retention of reaction mixture between the elements, making washing or even simple draining difficult. Also, if a finned stick is to be fabricated by molding, the number of fins may be limited by the ability to make a mold having the desired number of fins. The upper limit imposed by such considerations will depend on the size of the stick and the purpose for which it is to be used. For sticks to be used with reaction volumes on the order of about 1 ml, the preferred number of fins is at least eight. In a particularly preferred embodiment, eighteen fins, arranged radially around a central handle, are employed.

Additional advantages are provided by the present invention. The provision of an increased total surface area makes it possible to conduct quantitative determinations over a wider range of mobile reactant concentrations due to enhanced detectability at the lower end of the concentration range and increased binding capacity, such that proportionate response is possible at higher concentrations of the mobile reactant. Additionally, matrices of the present invention may be used to carry out direct, or sandwich assays of a quantitative sort. For this application, the increased binding capacity of the matrices of the present invention is necessary in order to immobilize materials over the entire range of potential concentrations, and not merely enough to provide a simple "yes-no" test. See, e.g., Bratu, et al., U.S. Pat. No. 3,826,619. For sandwich-type immunoassays, the range of antigen concentrations which may be measured quantitatively using a preferred embodiment of the present invention is very large, as demonstrated in Example 7. For competition-type immunoassays, the applicable range of the assay is determined by a complex interaction involving the matrix geometry, the amount and distribution of antibody immobilized on the matrix surface and the method of immobilization. The number, placement, size and shape of the matrix surface elements affects the kinetics of the immunochemical reaction, which in turn affects the amount of immobilized component necessary to provide a differential response with the amount of mobile component to be measured. Additionally, the stability of the bound component and the uniformity of its distribution are parameters affecting the design of the coated matrix. Advantageous results are obtained in a competition immunoassay with the use of coated matrices of the present invention by permitting the control of all significant factors affecting sensitivity, range and reproducibility. Additionally, the process of the present invention employs a reaction volume sufficiently large to permit a serum sample to be diluted with buffer to control the pH and reduce errors due to variation in the sample pH, or other factors such as protein concentration, and to provide constant volume, if necessary, from sample to sample. Devices of the present invention are not limited for use with a single defined reaction volume, since they do not depend upon fitting the reaction vessel within a close tolerance. No specific shape or size of reaction vessel is required. The matrix of the present invention need not fit snugly into the reaction vessel or even touch the vessel walls. The matrix elements having smooth plane or curved surfaces should be evenly disposed throughout the depth of the reaction fluid and in some systems, preferably extend above its surface, in order to provide an essentially uniform geometric relationship between mobile component molecules and the matrix surfaces over a wide range of reaction fluid volumes.

In both competitive and sandwich immunochemical assays, the length of time required to carry out the assay is dependent upon the rate at which the reaction approaches equilibrium. Reactions carried out by the process of the present invention approach equilibrium faster than conventional coated tube assays and may therefore be carried out in a shorter time. Furthermore, the use of a matrix of the present invention provides a very effective and precise means of starting and stopping reactions. This advantage becomes significant when it is necessary to carry out a large number of assays at one time. In such cases the time spent in the manipulations of starting and stopping the reaction is reduced to a minimum and can be more precisely controlled for all samples in the series. This feature is especially advantageous in comparison with coated tubes which must be decanted, sponges which must be squeezed or massaged to remove the last traces of the reaction mixture and particulate materials which must be centrifuged and decanted.

An additional advantage which stems from the enhanced reaction rate and increased capacity of the matrices of the present invention is that the same device can be used for both sandwich and competitive assays. When used in a quantitative competitive assay, the device provides a wide range of proportionate response as described previously and demonstrated in the examples.

Additional advantages result from the geometric configuration of the devices used in the process of the present invention. As stated hereinabove, the use of the devices results in an apparent enhancement of reaction rate not attributable to increased surface area per se. While an explanation for this phenomena is not presently known to applicants, it is suggested that providing a series of planar or curved surfaces extending throughout the depth of the liquid sample reduces the average distance between mobile reactants and the fixed component distributed on each surface and that such a reduction results in a faster overall reaction rate. In addition to faster reaction rates and the benefits which follow therefrom, the disclosed devices allow for greater uniformity of result. The geometric relationship between the mobile and fixed reactants is constant and reproducible from experiment to experiment, in contrast with particulate solid phase systems, wherein the particles have a tendency to settle at a rate which varies depending upon the particle size and particle size distribution. The process of the present invention is less susceptible to errors due to convection, which is a substantial difficulty associated with the use of coated tubes. The devices of the present invention are designed with substantially smooth surfaces to permit rapid draining of the reaction mixture when the matrix is removed from the solution. This feature allows the reactions to be terminated quickly, simplifies or eliminates washing steps and reduces potential contamination hazards when radioisotopes are employed. Many sources of potential human error are thereby eliminated. It is preferred to provide sticks having maximal surface smoothness, fabricated by a molding process, wherein the mold surfaces are polished, to a mirror smoothness. Maximum surface smoothness may be obtained by fabricating the matrix of molded plastic, using a mold having surfaces polished to mirror smoothness. That advantage is derived from the use of maximally smoothed surfaces may be contrary to expectation, since the rougher surfaces provide greater surface area. However, such maximally smoothed surfaces are employed in a preferred embodiment of the device in order to maximize removal of reaction fluid components from the matrix surfaces, and to minimize non-specific background interference.

From the foregoing, it will be appreciated that design of a properly functional matrix requires attention to all aspects and variables affecting the reaction to be conducted. In addition to providing a structural basis for enhanced reaction rates, operating convenience, minimized background interference and all the other advantages of the present invention, it is important to provide a coated surface having immobilized reactant distributed therein in such a manner that its reactivity is maximal. The immobilized component should be distributed as uniformly as possible over the surface. Gaps in the coating, which may be caused, for example, by an air bubble lodged on the matrix surface during the coating step, must be avoided. The immobilized reactant molecules must be exposed on the matrix surface, not buried in excess reactant or other carrier matter. Preferably the immobilized reactant should be bound to the matrix sufficiently strongly that no appreciable amount of reactant becomes desorbed, or otherwise removed during the incubation and washing steps of the reaction.

Embodiments having a plurality of individual projecting surfaces such as fins or rods are adaptable to methods for carrying out several tests at one time, by providing individual fins or rods with different materials immobilized upon them. The bundle of rods configuration shown in FIG. 3 is especially suitable for techniques of this sort. The rods may be made individually attachable and detachable so that the investigator may carry out any combination of assays appropriate to his purposes in a single reaction step, then measure the results individually.

In addition to the above-cited advantages of the insert matrix system in quantitative analysis, there are production advantages of commercial significance. In particular, techniques for immobilizing the fixed component can be adapted to apply to a large number of matrices at the same time, either in a batchwise or continuous manufacturing process. The consequent economies of scale and increased uniformity of product are clearly advantageous.

The matrices of the present invention may also have application in industrial quality control labs for routine chemical or enzyme-catalyzed reactions that may be conducted in a solid phase system. In addition, the devices may be useful for on-stream or batch production processes where it is desired to remove a specific substance from the reaction mixture. For example, matrices coated with ion-exchange resin could be used to remove specific ions from solution; specifically adsorbing proteins immobilized on matrices of the present invention could be used to remove contaminants, such as trace metals, from the production stream. Conventional catalysts may be used to coat the surfaces of the described insert matrices, for on-stream conversion of reactants, treatment of effluents and the like. The devices of the present invention, adapted to fit the appropriate size reaction vessel could be used for industrial scale as well as laboratory scale processes. Solid phase reactions with gaseous reactants, vapors, aerosols, particle suspensions and the like are also contemplated. The devices of the present invention may have special utility in flowing systems in which it is desirable to carry out reactions without reducing flow rate or introducing back pressure into the system.

BRIEF DESCRIPTION OF THE DRAWINGS

FIG. 1 illustrates the preferred embodiment of a solid phase matrix constructed in accordance with the invention.

FIG. 2 illustrates a modification of the embodiment illustrated in FIG. 1 in which a plurality of apertures are provided for increasing reactive surface area.

FIG. 3 illustrates another embodiment of the invention having a plurality of downwardly extending tines.

FIG. 4 illustrates another embodiment of the invention having concentric cylindrical surfaces.

FIG. 5 illustrates another embodiment of the invention having a continuous projecting surface in the form of a spiral ramp.

FIG. 6 illustrates another embodiment in the form of stacked discs.

FIG. 7 is a graph of results obtained in an experiment measuring antigen binding as a function of time, comparing devices of the present invention with a coated tube, at 37° C., as described in Example 2.

FIGS. 14(a) and 14(b) are scanning electron micrographs of matrix surfaces.

DETAILED DESCRIPTION OF THE DRAWINGS

Figure 8:
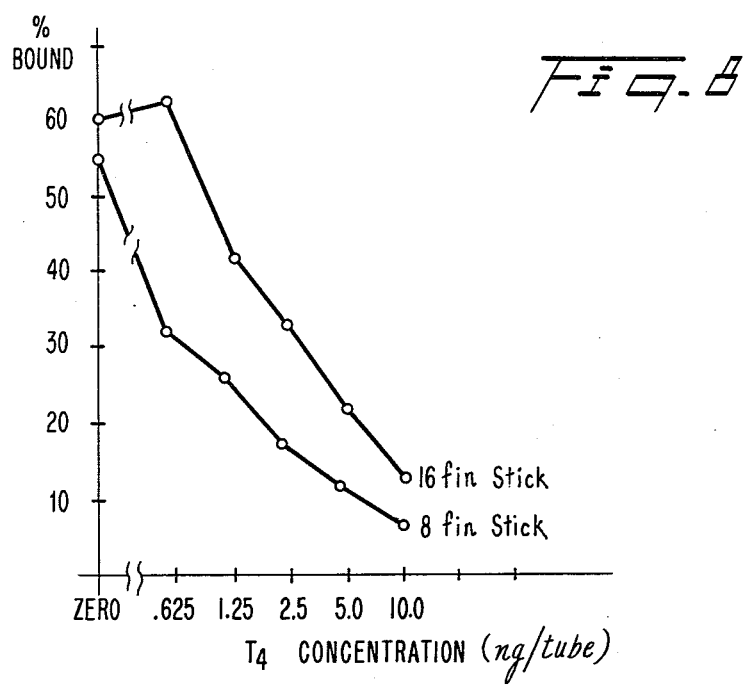
FIG. 8 is a graph of radioactively-labeled antigen binding as a function of total antigen concentration, comparing eight and sixteen-fin inserts for 1.5 hours at room temperature, as described in Example 3.

FIG. 1 illustrates the preferred geometric form of a solid phase insert 10 which is constructed in accordance with the invention. The insert has a plurality of equally-spaced fins 12 having outer extremities 14 which define a generally cylindrical volume which will fit into test tube 16 in close proximity to inner wall 18. The test tube 16 functions as a fluid receptacle for the sample which is to be assayed to determine the concentration or presence of components such as antibodies and antigens in accordance with the process of the invention described above. The insert has a vertically extending handle member 22 to which are attached the plurality of equally spaced radially projecting fins 12 which have a radius equal to or slightly less than the radius of the test tube. The rod functions as a handle. The bottom portion 26 of each fin is preferably shaped to conform the insert to the bottom of the test tube. The fins are preferably formed as part of a unitary structure which includes the center rod. However, the fins may be attached to the rod by means of physical connections such as a tongue and groove or by a suitable adhesive.

Figure 10:
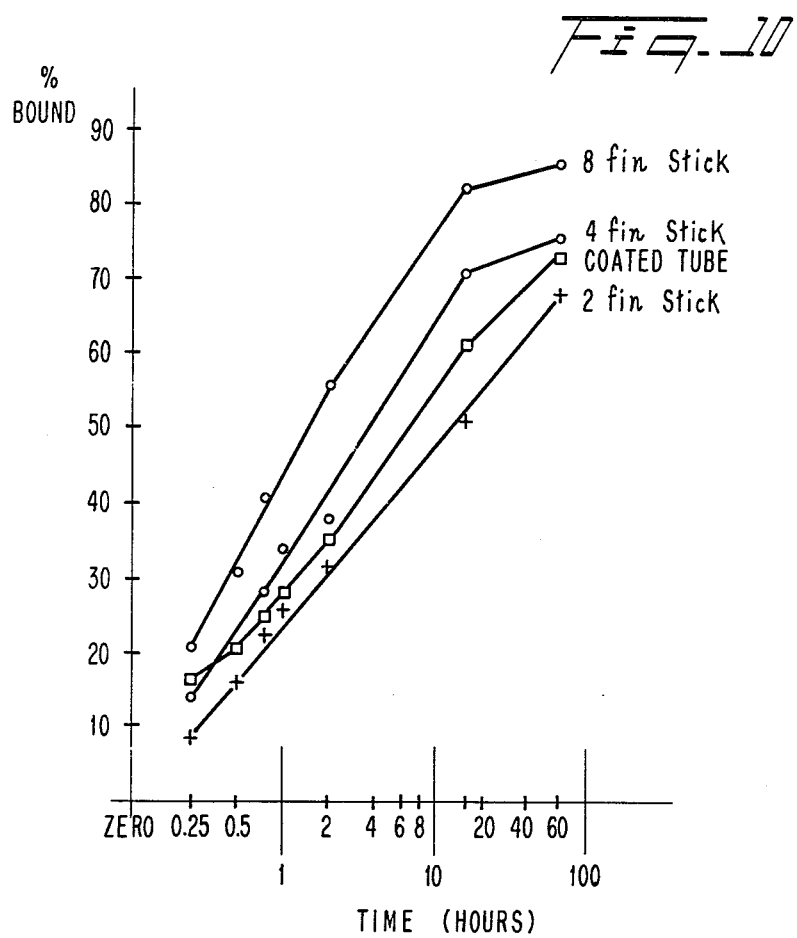
FIG. 10 is a graph of antigen binding as a function of time, comparing 2-, 4- and 8-fin inserts with a coated tube in a room temperature reaction, as described in Example 2.

While the embodiment of FIG. 1 illustrates eight, radially-projecting equally-spaced fins, other numbers and configurations of fins may be used to practice the invention. It has been found that an increase in the surface area of the insert, by providing an increased number of fins increases the reaction rate of the mobile and fixed components. Moreover, quite unexpectedly, it has been found that in many instances an eight-fin insert has a proportionally greater reaction rate in relation to a prior art coated tube than can be explained by the difference in their relative surface areas. See FIG. 7 and FIG. 10. Similar advantages have been observed with higher numbers of fins, such as 12, 16 and 18. In view of these observations, a preferred embodiment of the invention is a finned matrix, similar to that depicted in FIG. 1, having a plurality of fins ranging from 8 through 18. An 18-fin matrix has been constructed representing a most preferred embodiment of the invention. With finned devices of the type depicted in FIG. 1, the number of fins which is practical to employ will be limited by the increased difficulty of obtaining free drainage due to capillary adherance of the reaction fluid, especially in the region of the handle member where the fins approach each other at increasingly acute angles as the number of fins is increased.

Comparison of the data of FIG. 7 on the eight-fin insert with that of the prior art coated tube indicates that other considerations affect the interaction rate of the mobile and fixed components besides the area of exposed surface area coated with the fixed component. These considerations are not presently known to applicants, though it is now believed that the lessening of average diffusion distance in the eight-fin insert over that in the coated tube is at least one such consideration.

FIG. 2 illustrates another embodiment of the invention which is identical to the embodiment illustrated in FIG. 1 in all ways except that a plurality of apertures 28 are provided in the fins to increase the surface area of the fixed component which is wetted by the sample being assayed. The apertures 28 may extend completely through the fins. As illustrated, the apertures may be circular or oblong, or may be of any other shape. To increase the area of the insert by inclusion of circular apertures, the radius of the apertures must be less than twice the wall thickness 30.

In FIG. 3 an alternate embodiment of the invention is shown having a handle 50 to which is attached a flat disc 52 cut to have a diameter slightly smaller than a test tube into which the device is designed to fit. A plurality of downwardly projecting tines 54 is attached to the disc 52. The bottom ends of the tines 56 may be of uniform length or of graduated length to conform to the round bottom of a test tube. The tines 54 are depicted as cylindrical in cross-section but they may have other cross-sectional shapes in other embodiments. The tines 54 may be individually attachable and detachable from the disc 52. The embodiment of FIG. 3 is especially suited for complex analyses involving several different test reactions in the same sample, in addition to its general usefulness in solid phase reactions.

FIG. 4 shows another embodiment of the invention having a central rod 22 to which is attached by means of radially projecting struts 64 a plurality of concentric cylindrical surfaces. FIG. 4 depicts a pair of such surfaces 60 and 62. In order to accommodate the rounded bottom of the test tube, the inner concentric cylinder 60 projects below the outer cylinder 62 and the central rod 22 projects slightly beyond the inner cylinder 60. A set of lower struts 66 provides rigidity for the lower end of the structure and also facilitates free drainage of fluid.

FIG. 5 shows another embodiment of the invention having a generally radially projecting surface in the form of a spiral ramp 36 winding around a central core 32 which is attached to a handle 22. The device provides a continuous essentially horizontal surface 36 and a vertical surface 34 formed by the ramp and its outer face respectively. The slope of the ramp provides for free drainage of the reaction fluid by gravity when the device is removed from the reaction fluid. The embodiment of FIG. 5 is especially suitable for reactions in which stirring is desired. The device is tapered at the lower end 38 to provide a conforming fit with the bottom of a test tube receptacle as shown in FIG. 1.

FIG. 6 is another embodiment of the invention having a plurality of horizontally disposed discs 42 attached to a central handle 22 having essentially parallel upper and lower surfaces 44 and vertical edges 46. The discs are contoured at the bottom of the rod 48 to conform to the rounded bottom of the test tube. While the geometric configuration of FIG. 6 may be used to practice the invention, it and similar embodiments lacking freely drainable surfaces require the expenditure of proportionately more laboratory time because of washing requirements that are not presented by the freely drainable geometric configurations of FIGS. 1-5.

Other geometric configurations of the insert than those illustrated in FIGS. 1-6 may be utilized to practice the invention. These geometric configurations should preferably have vertically oriented smooth surfaces in contact with the liquid sample in order to facilitate drainage by gravity upon their removal from the test tube. Any geometric configuration which has a freely drainable relatively large surface area may be used to practice the invention. The larger the wettable surface area, the faster the interaction rate of the mobile and fixed components.

Prior to use of an insert in accordance with the invention by placing it in a fluid sample which contains a mobile component to quantitatively or qualitatively be measured, all surfaces are coated with the fixed component as has been discussed supra. Large numbers of inserts may be coated at one time to reduce the cost of manufacturing to a point to make discarding of used inserts economical.

The insert may be fabricated from virtually any stable water-insoluble material, including, for example, polymethacrylate, polypropylene and polystyrene.

FIG. 14(a) is a scanning electron micrograph of the surface of a preferred embodiment, eighteen-fin matrix molded in a polished mold. Magnification: 300×; scanning angle: 45°.

FIG. 14(b) is a scanning electron micrograph of the surface of a prototype matrix, molded of the same plastic material used in FIG. 14(a), but with an unpolished mold. Magnification: 300×; scanning angle: 45°.

The process of conducting a solid phase reaction employing a reactant affixed to an insert will next be described in specific examples, in order to more clearly reveal the characteristics and utility of the invention.

EXAMPLE 1

Matrices of the present invention in the form of two-fin, four-fin and eight-fin sticks of polymethacrylate were prepared for use in the solid phase reaction in comparison with a prior art polystyrene coated tube. The sticks were constructed essentially as depicted in FIG. 1 except that the fins were not rounded on the bottom end and therefore did not extend into the rounded bottom part of the reaction tube. The measured surface area for each configuration of the solid phase is given as follows:

| Solid Phase Configuration | Surface Area |
|---|---|
| Coated Tube | 899 mm² |
| Two-fin Insert | 452 mm² |
| Four-fin Insert | 660 mm² |
| Eight-fin Insert | 1075 mm² |

The reaction was an antigen-antibody reaction between $^{125}$I-Thyroxine (T4) and rabbit anti-Thyroxine antibody. The antibody was used as the fixed component and the radioactive antigen was used as the mobile component.

In order to immobilize the antibody on the above solid phase surfaces, a 2.5% solution of glutaraldehyde was diluted with an equal volume of 0.5 M sodium carbonate buffer having a pH of 9.5. The solid phase surfaces were immersed in the glutaraldehyde solution for at least 3 hours at room temperature, then washed with water. The glutaraldehyde treated surfaces were then immediately reacted with a 1:1000 dilution of rabbit anti-T4 serum in 0.5 M sodium carbonate pH 9.5, for 12 hours at room temperature.

The surfaces were then washed with water and stored in phosphate-buffered saline composed of 0.006 M NaH$_2$PO$_4$, 0.024 M K$_2$HPO$_4$ and 0.15 M sodium chloride, pH 7.4, with added 0.1% bovine serum albumin and sufficient merthiolate to release any T4 bound to serum protein, the complete mixture hereinafter referred to as T-4 buffer.

The reactions were carried out by incubating the coated surface bearing immobilized anti-Thyroxine antibody with a small amount of $^{125}$I-Thyroxine in a total reaction volume of 1.6 ml. Samples were incubated for various lengths of time at room temperature. The results are shown in the following table:

| | | Percent of Label Bound at Indicated Time | | | | | | |
|---|---|---|---|---|---|---|---|---|
| Present Invention Matrices | Prior Art Matrix | 15 min. | 30 min. | 45 min. | 1 hr. | 2 hrs. | 16 hrs. | ~65 hrs. |
| 2-fin stick | | 9.3 | 17.4 | 21.7 | 26.7 | 31.9 | 52.0 | 68.2 |
| 4-fin stick | | 14.2 | 22.2 | 28.3 | 34.2 | 38.1 | 70.6 | 75.7 |
| 8-fin stick | | 20.4 | 31.1 | 40.3 | 36.6 | 58.7 | 81.4 | 85.3 |
| | Coated Tube | 16.1 | 21.8 | 24.4 | 28.5 | 36.4 | 60.6 | 73.6 |

The reaction characteristics of finned inserts vis a vis the coated tube are demonstrated by the foregoing experiment. Initially it should be noted that the $^{125}$I-Thyroxine was about 85%–90% pure so that the maximum binding which could be achieved was about 85%–90%. Therefore it can be seen that the eight-fin insert had approached equilibrium by 16 hours. More significantly, the four-fin insert, while having only about three quarters the surface area of the coated tube, immobilized antigen at a slightly faster rate than the coated tube. Also, the two-fin insert had immobilized more antigen per unit surface than had the coated tube.

EXAMPLE 2

The reaction procedure of Example 1 was carried out except that reactions were run for various lengths of time at room temperature and at 37° C. The results are plotted in FIG. 7 at 37° C. and FIG. 10 at room temperature. It can be seen that the four-finned insert, despite having less surface area than the coated tube, was able to bind a higher percentage of antigen throughout most of the course of the reaction at room temperature. At 37° C., the four-fin insert did not bind more antigen than the coated tube. However, the eight-fin insert, despite having only 1.2 times the surface area of the coated tube had bound nearly 1.6 times as much antigen by the end of 60 minutes incubation.

EXAMPLE 3

Figure 11:
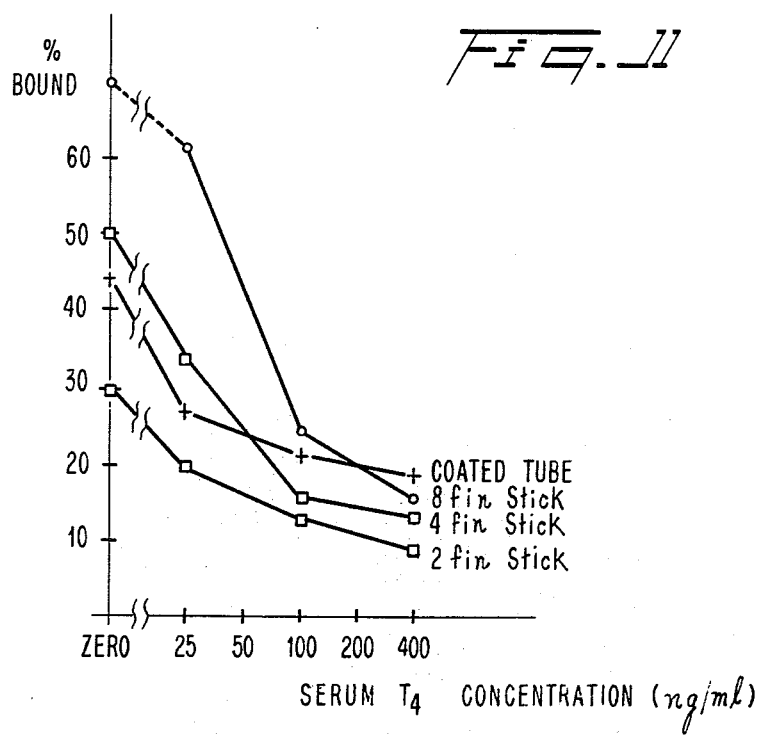
FIG. 11 is a graph of radioactively-labeled antigen binding as a function of total antigen concentration, comparing 2-, 4- and 8-fin inserts with a coated tube, in a 3 hour incubation at 37° C., as described in Example 3.

The response of finned inserts to increasing concentration of antigen was compared with that of coated tubes. The reactions were run essentially as described in Example 1 with the exception that the concentration of antigen was varied by the addition of unlabeled Tyroxine protein-based standards while maintaining the concentration of $^{125}$I-Thyroxine constant. Antigen concentration was varied from 25 to 400 nanograms Thyroxine per ml. serum, based on a sample volume of 0.025 ml. In FIG. 11, two-, four-, and eight-fin matrices were compared with a coated tube in a 3 hour incubation at 37° C., in a total reaction volume of 1.725 ml. The reaction buffer was the T4 buffer of Example 1. While the finned sticks of this invention appeared to follow a family of curves of the same general shape, the coated tube was distinctive in its behavior, again indicating that reaction rate appeared to differ between the inserts and the coated tube. It can also be seen that the curves for the fin inserts, particularly the four- and eight-fin inserts, followed steeper slopes over a wider range of antigen concentration than did the curve for the coated tube. The finned inserts are therefore able to provide a better differential response over a wider range of antigen concentration.

In FIG. 8, results from a similar experiment are shown, comparing the behavior of eight-fin and sixteen-fin inserts. In this experiment, the matrices were incubated 1.5 hours at room temperature in a total reaction volume of 1.425 ml for the 8-fin insert and 1.025 ml for the 16-fin insert. The sixteen-fin insert would be advantageous for quantitative analytic purposes because of its generally greater response and the generally steeper slope of its response curve at most concentrations of antigen.

Figure 9:
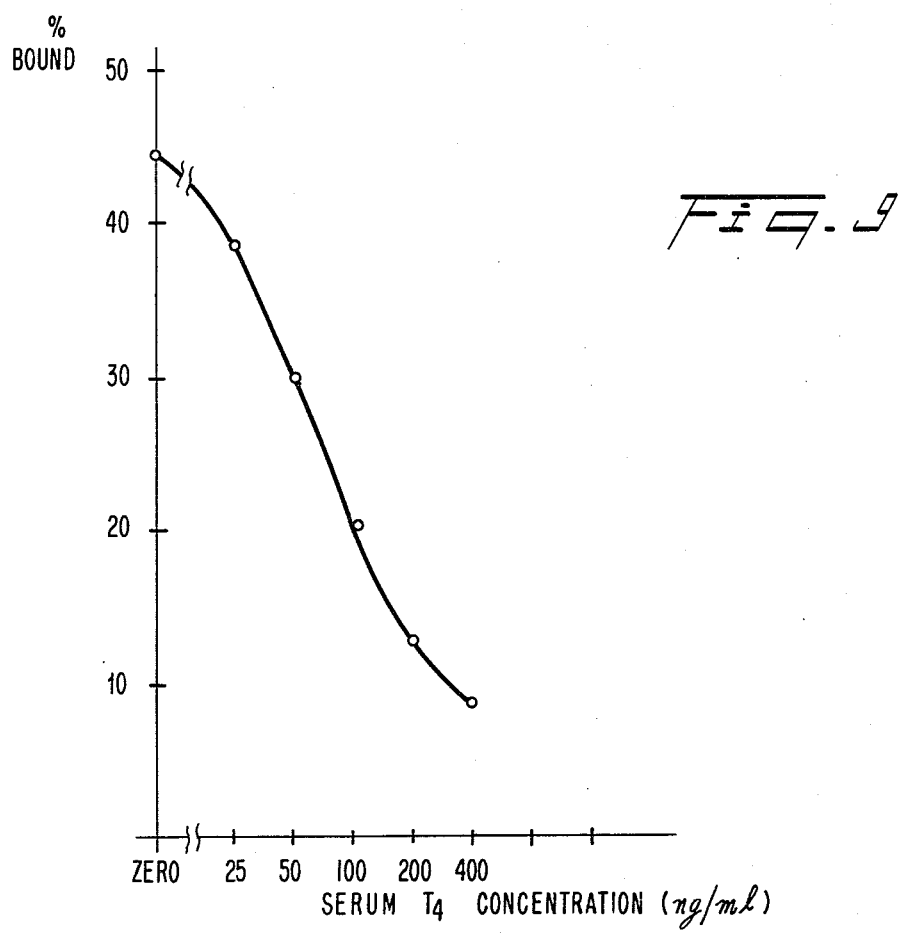
FIG. 9 is a graph of radioactively-labeled antigen binding as a function of total antigen concentration, using an eight-fin insert in a 45 minute reaction at 22° C., as described in Example 3.

FIG. 9 shows the results of a similar experiment, using an eight-fin matrix in a 45 minute reaction at 22° C. Total reaction volume was 1.325 ml and sample volume was 0.025 ml. Under these conditions, the eight-fin matrix gave a usable response over the entire concentration range tested, in a relatively rapid reaction.

EXAMPLE 4

A comparison was made between an 8-fin stick and a coated tube in an immunochemical assay for insulin. Guinea pig antiserum against insulin was immobilized on the surfaces of tubes and sticks by the technique described in Example 1. The reaction was carried out as described in Example 1 except that insulin was used as the antigen. Each reaction tube contained an identical amount of $^{125}$I-labeled insulin together with an amount of unlabeled insulin in phosphate-buffered saline containing bovine serum albumin. The total reaction volume for both systems was 1.3 ml containing 300 μl unlabeled insulin standard and 1 ml of phosphate-buffered saline as in Example 1 containing 50 mg/ml bovine serum albumin. The data, expressed as percent of total label bound to the reactive surface, is given in the following table.

| | Percent of Labeled Antigen Bound | | | | | |
|---|---|---|---|---|---|---|
| | 6.25 μUnits | | 25 μUnits | | 200 μUnits | |
| Time (hours) | 8-fin stick of the invention | coated tube | 8-fin stick of the invention | coated tube | 8-fin stick of the invention | coated tube |
| 1 | 35 | 12 | 33 | 12 | 18 | 6 |
| 2 | 43 | 19 | 33 | 14 | 25 | 8 |
| 3 | 51 | 20 | 44 | 16 | 30 | 7 |

The percent of binding observed with the 8-fin stick was generally more than twice the amount observed with the coated tube although the former had only about 1.2 times the surface area of the latter, as shown in Example 1.

EXAMPLE 5

Figure 13:
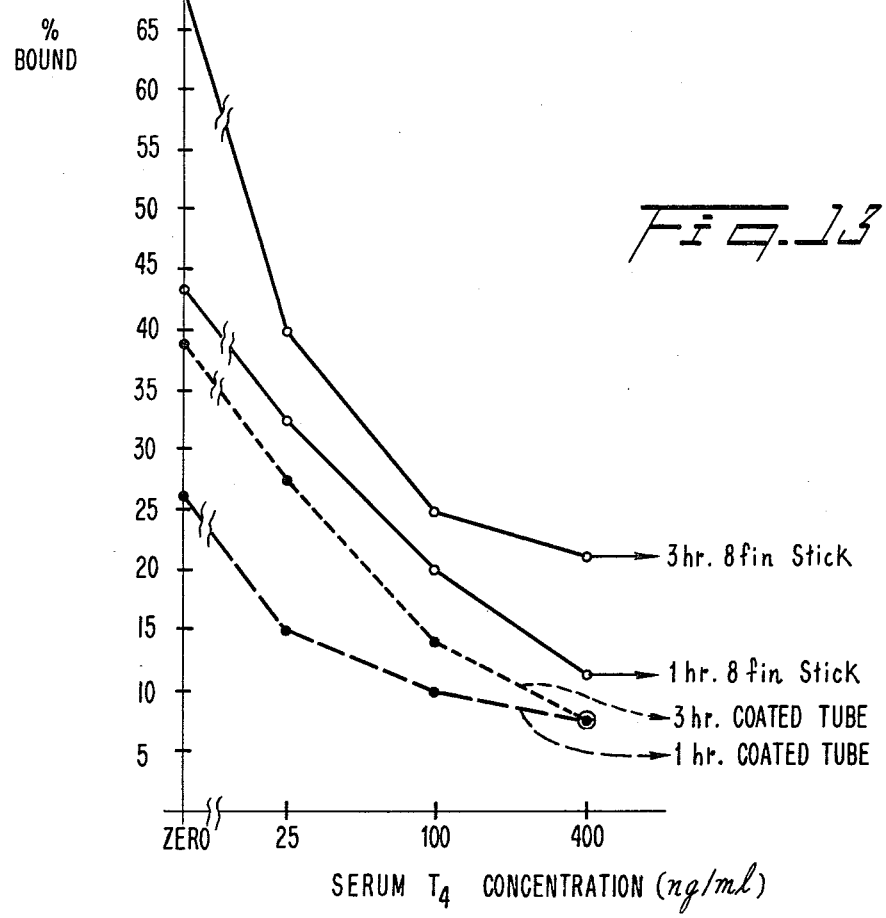
FIG. 13 is a graph of radioactively-labeled antigen binding as a function of total antigen concentration, comparing 8-fin inserts and coated tubes constructed of the same material, for the indicated reaction time at room temperature, as described in Example 5.

The following experiment was designed to control for the effects of different surface area, lack of fins extending into the rounded bottom portion of the reaction tube, and possible differences in binding affinity between polymethacrylate and polystyrene, in a comparison between the 8-fin stick and coated tube solid phases. The reaction was carried out as described in Example 3 using incubations for the indicated times at room temperature. Both the tubes and the sticks used in this experiment were constructed of polymethacrylate. The tubes were provided with a flat bottom and a sufficiently large coated surface area to provide a surface area equal to that of the coated stick. The data are shown in FIG. 13. It can be seen that the elimination of the foregoing variables did not substantially alter the general result of the previous examples: that binding to the coated sticks of this invention generally occurs more rapidly than on coated tubes even when the coated surface area is the same for both.

EXAMPLE 6

Figure 12:
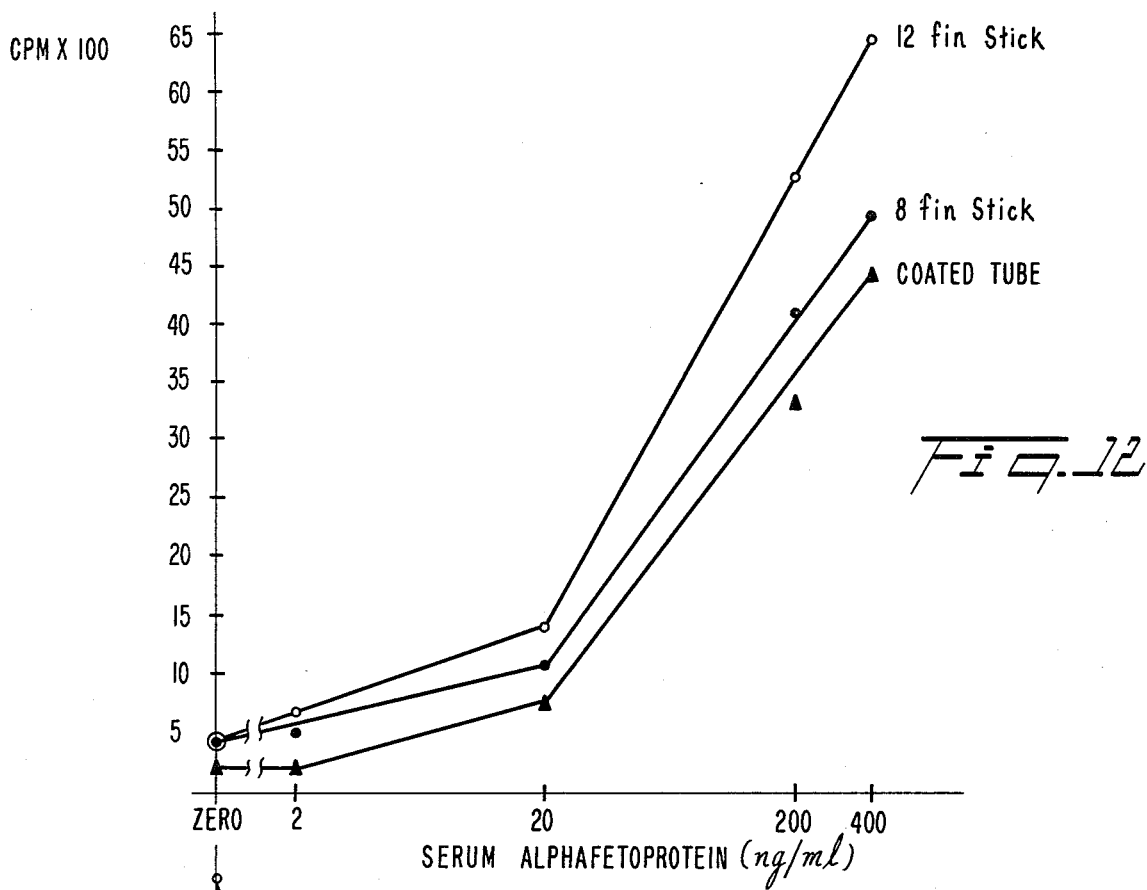
FIG. 12 is a graph of radioactively-labeled antibody binding as a function of the antigen concentration in a sandwich assay comparing 8- and 12-fin inserts with a coated tube in a two-hour incubation with antigen at 37° C., followed by a 1 hour, 15 minute incubation with antibody at 37° C., as described in Example 6.

The results of a sandwich assay for alpha fetoprotein, comparing 8-fin and twelve-fin matrices with a coated tube, are shown in FIG. 12. Antibody to alpha fetoprotein was immobilized by adsorption. The 8- and 12-fin sticks were immersed in 1.5 ml of a solution containing 18 μg alpha fetoprotein antibody per ml of 0.5 M sodium carbonte buffer, pH 9.5, and incubated for two hours at 37° C. Polystyrene tubes were coated in a similar manner by placing 1.5 ml of the same antibody solution into the tube and incubating under the same conditions. At the end of the incubation period the tubes and matrices were rinsed and placed in phosphate buffered saline, pH 7.4, containing 10 mg/ml bovine serum albumin for one hour. The tubes and matrices were rinsed again and the assay buffer was added to the tubes containing the 8-fin sticks, total volume 1.5 ml, 12-fin sticks, total volume 1.1 ml, and to the coated tubes, total volume 1.5 ml. The assay buffer was identical to that previously described as T4 buffer in Example 1 except that merthiolate was omitted and the content of bovine serum albumin was 10 mg/ml. Alpha fetoprotein was added to the reaction tubes to provide final concentrations of 1 ng, 2 ng, 20 ng, 200 ng and 400 ng per ml of serum, based on a sample volume of 0.1 ml. Immediately after the addition of alpha fetoprotein, 100 μl of $^{125}$I-labeled antibody to alpha fetoprotein was added, providing 40,000 cpm total. The mixture was incubated at 37° C. for one hour 15 minutes. After the incubation the matrices were removed and the tubes decanted. Both tubes and matrices were rinsed briefly and the radioactivity bound thereto was counted in a gamma counter.

The fin stick matrices of the present invention gave a differential response of greater magnitude at all concentrations of antigen than that observed with the coated tube, a matter of especial significance at the lower range of concentrations tested. The 12-fin matrix gave a response of greater magnitude at all concentrations of antigen tested and also provided a somewhat greater differential response.

EXAMPLE 7

An immunoassay for thyroxine stimulating hormone (TSH) was carried out using a preferred embodiment of the present invention. Matrices in the form essentially as depicted in FIG. 1 having eighteen fins were fabricated of molded polypropylene, using a mold with polished surfaces to impart maximal smoothness to the plane fins attached to the handle member.

The matrix was coated with anti-TSH antibody by immersing the finned portion in 1.2 ml of a solution containing approximately 1 μg purified antibody and 10 μg bovine serum albumin in 0.01 M potassium phosphte buffer, pH 9.0, for 2 hours at 37° C. The matrix was next washed with water and transferred to a solution of glutaraldehyde, 0.005% (v/v) in 0.01 M potassium phosphate buffer, pH 9.0 and incubated for 2 hours at 37° C. The matrix was again washed with water, then washed for 10 minutes with a slowly flowing aqueous solution of Triton X-100, 2 mg/ml,[1] at pH 1.85, washed with tap water and stored in phosphate buffered saline at 4° C. until use.

[1] Trademark, Rohm & Haas Corp.

Matrices prepared as described were immersed in tubes containing 0.2 ml of TSH standards in amounts varied from tube to tube, and 0.2 ml of $^{125}$I-labeled anti-TSH antibody yielding 174,535 total counts per minute per tube. A reaction of this type, where the mobile component of the solid phase reaction and the indicator are incubated simultaneously with the solid phase reactant, is termed a simultaneous sandwich assay. One set of the matrices was incubated for 2 hours at 37° C., and a second set was incubated for 3 hours at 37° C. Total reaction volume was 0.4 ml.

The results are shown in the following table.

| TSH (no. Units/ml) | 2 hr. incubation cts/min bound | Average % total cts bound: corrected for 65% antibody avidity | 3 hr. incubation cts/min bound | Average % total cts bound: corrected for 65% antibody avidity |
| --- | --- | --- | --- | --- |
|  | 1036 |  | 1100 |  |
| 0 | 1207 | 0.99 | 1098 | 0.97 |
|  | 1603 |  | 1544 |  |
| 0.75 | 1621 | 1.46 | 1767 | 1.46 |
|  | 1716 |  | 2124 |  |
| 1.5 | 2080 | 1.67 | 2171 | 1.89 |
|  | 2352 |  | 3017 |  |
| 3.1 | 2388 | 2.09 | 2958 | 2.63 |
|  | 3652 |  | 4346 |  |
| 6.2 | 3615 | 3.20 | 4463 | 3.88 |
|  | 6330 |  | 7207 |  |
| 12.5 | 6297 | 5.57 | 7506 | 6.48 |
|  | 11020 |  | 12160 |  |
| 25 | 10095 | 9.31 | 12175 | 10.73 |
|  | 17191 |  | 20606 |  |
| 50 | 18943 | 15.93 | 21983 | 18.77 |
|  | 31707 |  | 35447 |  |
| 100 | 32014 | 28.08 | 36223 | 31.59 |

The results of duplicate experiments indicate a highly reproducible reaction system. The relatively small increase in the amount of label bound as a result of an additional one hour's incubation indicates a rapid reaction rate in which most binding has already occurred in the first two hours. The system has the sensitivity to measure amounts to TSH antigen as low as 1.5 micro units/ml while having at the same time the capacity to measure up to at least 100 micro units/ml.

EXAMPLE 8

A competition type assay using a preferred embodiment 18-fin matrix, as described in Example 7, is disclosed. The matrix was coated with anti-Digoxin antibody, essentially by the procedure for coating a matrix described in Example 7. Sufficient antibody was present to yield approximately 250 ng antibody per matrix.

The competition reaction fluid contained unlabeled Digoxin at 0, 0.5 or 6.0 ng/ml and 16163 total cts/min [$^3$H] Digoxin in 0.01 M potassium phosphate buffer, pH 7.5. Total reaction volume was 1.2 ml. The reaction fluid was incubated in the presence of the matrix at 37° C. or at room temperature for the time indicated in the following table. The results are expressed as percent of labeled Digoxin bound, averaging the results of duplicate runs.

| Reaction Temp | Incubation Time (minutes) | Digoxin Concentration (ng/ml) | | |
| --- | --- | --- | --- | --- |
|  |  | 0 | 0.5 | 6.0 |
| 37° C. | 10 | 41.0% | 30.3% | 5.5% |
|  | 30 | 57.0% | 41.1% | 7.9% |
|  | 90 | 66.2% | 43.1% | 7.9% |
| Room Temp. | 10 | 33.5% | 25.6% | 6.5% |
|  | 30 | 56.3% | 34.3% | 5.9% |
|  | 90 | 58.5% | 43.7% | 6.1% |

At the 0.5 ng/ml level, maximum discrimination was obtained with a 90-minute incubation at 37° C., although readily measurable discrimination was obtained with 10-minute incubations either at 37° C. or at room temperature.

EXAMPLE 9

A simultaneous sandwich assay for TSH as described in Example 7, was carried out using a parallel fin matrix, not depicted herein, having six fins and a flat bottom, molded in a non-polished mold, as described in Example 10.

Antibody against TSH was immobilized by adsorption in 0.01 M potassium phosphate, pH 9.0, containing 1.5 μg/ml anti-TSH antibody protein and 15 μg/ml IgG for 1.5 hours at 37° C. After the adsorption period, the matrices were washed twice with phosphate-buffered saline containing 10 μg/ml bovine serum albumin.

The reaction was carried out in the process of the indicated amounts of TSH, using [$^{125}$I]-labeled anti-TSH antibody indicator reagent, total cts/min, 127,000. The reaction buffer was phosphate-buffered saline and the reactions were carried out for the indicated times at 37° C. To facilitate drainage and washing of the device, the matrix was removed from the reaction fluid, blotted briefly by setting the flat bottom against an absorbant pad, then centrifuged in a tube containing a glass bead to support the matrix, in order to remove the last traces of reaction fluid. The matrix was then immersed in a wash buffer and the process repeated twice. The results are shown in the following table.

| TSH | Percent $^{125}$I-labeled bound corrected for 75% avidity | | |
|---|---|---|---|
| (μ Units/ml) | 1 hr. | 2 hrs. | 16 hrs. |
| 0 | 2.2% | 2.6% | 4.4% |
| 1 | | 2.7% | 4.4% |
| 25 | | 4.9% | 5.1% |
| 50 | 5.8% | 7.6% | 7.2% | while the foregoing is one of the less preferred embodiments, it is seen that even used in this manner, the device and method of the invention are effective.

EXAMPLE 10

An eighteen-fin preferred embodiment matrix such as that used in Examples 7 and 8 was examined under a scanning electron microscope to determine the effect on surface smoothness, of the polished mold used in its fabrication. For comparison, the surface of a prototype matrix, molded of the same plastic material in an unpolished mold, was also examined. FIG. 14(a) shows the surface, magnified 300× at a scanning angle of 45°, of the polished-molded matrix. FIG. 14(b) shows the surface of the unpolished-molded matrix, viewed under the same conditions. The use of a mold having mirror-polished surfaces resulted in a markedly increased surface smoothness.

Interestingly, while both surfaces are substantially smooth from a sensory viewpoint and hence are within the scope of the invention, it currently appears that the matrix made in the polished mold is preferred.

Use of the matrix of the preferred embodiment, such as that viewed in FIG. 14(a), has resulted in highly reproducible results having a low background of non-specific binding.

EXAMPLE 11

The solid phase matrix described in Example 7 was used in an enzyme-linked immunoassay for ferritin and the results compared with those obtained using a coated tube. The assay method was a sandwich assay in which the 18-fin matrix, or the reaction tube, was coated with antibody to ferritin and allowed to react in a reaction fluid containing a test sample of ferritin. The matrix, or tube, was then separated from the reaction fluid, washed and incubated with an anti-ferritin antibody conjugated with an enzyme. Alternatively, a simultaneous sandwich assay could be performed, wherein the ferritin and anti-ferritin antibody-enzyme conjugates are incubated together with the immobilized anti-ferritin antibody. In either case, the presence of ferritin permitted the binding of antibody-enzyme conjugate to the solid phase in amounts proportionate to the amount of ferritin present. The amount of antibody-enzyme conjugate bound was measured by the introduction of a chromogenic enzyme substrate whereby the action of the bound enzyme moiety of the conjugate produced a color change. The amount of color change was proportional to the amount of conjugate bound.

In comparing the results of such an assay using either the 18-fin matrix or a coated tube, it was observed that, for the same incubation time, the use of the 18-fin matrix resulted in the order of eight or more times the optical density produced with the use of a coated tube.

Having thus described the invention with particular reference to the preferred forms thereof, it will be obvious to those skilled in the art to which this invention pertains after understanding the invention, that changes and modifications may be made without departing from the spirit and scope of the invention as defined by the appended claims.

We claim:

1. A process for determining the amount of mobile component contained in a fluid sample which reacts with a fixed component immobilized on a solid phase insert matrix to produce a measurable change which is a function of the amount of the mobile component comprising the steps of:
   (a) providing a fluid receptacle containing a fluid sample having an unknown amount of the mobile component which is to be measured,
   (b) providing a removable impermeable unitary insert matrix comprising a handle member having attached at one end a plurality of elements having essentially smooth plane or curved surfaces so arranged with respect to one another and the handle member and of a size and shape such that when said matrix is inserted into said fluid receptacle, said matrix extends substantially throughout the depth of said fluid sample and the average diffusion distance of molecules of said mobile component to the surfaces of said elements is greatly reduced relative to the average diffusion distance of molecules of said mobile component to the fluid receptacle when no matrix is present therein, and having the fixed component immobilized on the surfaces of said elements, capable of reacting with said mobile component at a rate or to an extent measurable as a function of the concentration of said mobile component,
   (c) placing the insert in the fluid receptacle to cause contact between the fixed component of the insert matrix with the mobile component of unknown amount contained in the fluid sample for a given time interval to permit a reaction to occur, and
   (d) measuring the change which is a function of the concentration of the mobile component to determine the amount of the mobile component.

2. The process of claim 1 wherein the fixed component is an antibody, the mobile component is an antigen and the reaction is the binding of the antigen to the antibody.

3. The process of claim 2 wherein at least a portion of the antigen contains a radioactive label and the amount of radioactivity bound to the antibody immobilized on the insert is measured to determine the amount of antigen bound.

4. The process of claim 2 wherein step (d) comprises the steps of:
   immersing the insert having antigen bound thereon in a second fluid containing a reagent capable of reacting specifically with the bound antigen, and
   measuring the amount of reagent which has reacted with the bound antigen, in order to measure the amount of antigen bound, in order to measure the amount of antigen present in the fluid sample.

5. The process of claim 4 wherein the reagent comprises a radioactively tagged antibody.

6. The process of claim 1 wherein the fixed component is an enzyme and the mobile component is a substance capable of undergoing a chemical transformation catalyzed by the enzyme.

7. The process of claim 1 wherein the mobile component is an enzyme and the fixed component is a substance capable of undergoing a chemical transformation catalyzed by the enzyme.

8. The process of claim 1 wherein the solid phase insert matrix comprises a central rod and a plurality of fin-like projections extending outwardly from said rod along a portion of the length of said rod, said fins having outer edges conforming approximately to the shape of the fluid receptacle.

9. A process according to claim 1 wherein the solid phase insert matrix comprises a central rod and a plurality of fin-like projections extending outwardly from the rod along a portion of the length of the rod, said fins having a plurality of apertures therethrough providing increased total matrix surface area and having outer edges conforming approximately to the shape of the fluid receptacle.

10. A process according to claim 1 wherein the solid phase matrix comprises a central rod attached at one end to one face of a flat disc, at its center, said disc having attached on its opposite face a plurality of essentially equally spaced tines, oriented parallel to the axis of the central rod.

11. A process according to claim 1 wherein the solid phase matrix comprises a central rod at the axis and a plurality of concentric cylinders interconnected to each other and to the central rod by means of radial projections.

12. A process according to claim 1 wherein the solid phase matrix comprises a central rod at the axis and a continuous surface projecting therefrom in the form of a spiral ramp.

13. A process according to claim 1 wherein the solid phase matrix comprises a central rod at the axis and a plurality of uniformly spaced planar discs coaxial to the rod and to each other, the plane of said discs being approximately perpendicular to the central rod.

14. A method for producing a measurable reaction in a fluid sample in a reaction vessel comprising:

providing a fixed component immobilized on a solid phase matrix, said matrix comprising a handle member having attached at one end a plurality of elements having essentially smooth plane or curved surfaces so arranged with respect to one another and the handle member and of a size and shape such that when said matrix is inserted into said reaction vessel said matrix extends substantially throughout the depth of said fluid sample and the average diffusion distance of molecules in said fluid sample to the surfaces of said elements is greatly reduced relative to the average diffusion distance of said molecules in said fluid sample to the reaction vessel when no matrix is present therein, said fixed component being immobilized on the surfaces of said elements, providing a mobile component capable of reacting measurably with the fixed component, and placing the fixed component in reactive proximity with the mobile component, thereby producing a measurable reaction.

15. The method of claim 14 wherein the solid phase matrix comprises a central rod and a plurality of fin-like projections extending outwardly from said rod along a portion of the length of said rod.

16. The method of claim 14 wherein the solid phase matrix comprises a central rod attached at one end to one face of a flat disc, at its center, said disc having attached on its opposite face a plurality of essentially equally spaced times, oriented parallel to the axis of the central rod, said tines being sized to conform approximately to the shape of the fluid receptacle.

17. The matrix of claim 16 having means for individually attaching and detaching the tines.

18. The method of claim 14 wherein the solid phase matrix comprises a central rod at the axis and a plurality of concentric cylinders interconnected to each other and to the central rod by means of radial projections.

19. The method of claim 14 wherein the solid phase matrix comprises a central rod and a plurality of fin-like projections extending outwardly from the rod along a portion of the length of the rod, said fins having a plurality of apertures therethrough providing increased total matrix surface area and having outer edges conforming approximately to the shape of the fluid receptacle.

20. The method of claim 14 wherein the solid phase matrix comprises a central rod attached at one end to one face of a flat disc, at its center, said disc having attached on its opposite face a plurality of essentially equally spaced tines, oriented parallel to the axis of the central rod.

21. The method of claim 14 wherein the solid phase matrix comprises a central rod at the axis and a plurality of concentric cylinders interconnected to each other and to the central rod by means of radial projections.

22. The method of claim 14 wherein the solid phase matrix comprises a central rod at the axis and a continuous surface projecting therefrom in the form of a spiral ramp.

23. The method of claim 14 wherein the solid phase matrix comprises a central rod at the axis and a plurality of uniformly spaced planar discs coaxial to the rod and to each other, the plane of said discs being perpendicular to the central rod.

24. A solid phase matrix for insertion into a reaction vessel containing a fluid sample comprising molecules of a mobile component to be measured or detected, which matrix comprises, (1) a handle member having attached at one end a plurality of elements having essentially smooth plane or curved surfaces so arranged with respect to one another and the handle member and of a size and shape such that when said matrix is inserted into said reaction vessel said matrix extends substantially throughout the depth of said fluid sample and the average diffusion distance of said molecules of a mobile component to the surfaces of said elements is greatly reduced relative to the average diffusion distance of said molecules of a mobile component to the reaction vessel when no matrix is present therein, and (2) a fixed component immobilized on the surfaces of said elements, capable of reacting with said mobile component at a rate or to an extent measurable as a function of the concentration of said molecules of a mobile component.

25. The solid phase matrix of claim 24 comprising a central rod and a plurality of fin-like projections extending outwardly from said rod along a portion of the length of said rod.

26. The solid phase matrix of claim 24 comprising a central rod and a plurality of fin-like projections extending outwardly from the rod along a portion of the length of the rod, said fins having a plurality of apertures therethrough providing increased total matrix surface area relative to said projections lacking said apertures.

27. The solid phase matrix of claim 24 comprising a central rod attached at one end to one face of a flat disc, at its center, said disc having attached on its opposite face a plurality of essentially equally spaced tines, oriented parallel to the axis of the central rod.

28. The solid phase matrix of claim 24 comprising a central rod at the axis and a plurality of concentric cylinders interconnected to each other and to the central rod by means of radial projections.

29. The solid phase matrix of claim 24 comprising a central rod at the axis and a continuous surface projecting therefrom in the form of a spiral ramp.

30. The solid phase matrix of claim 24 comprising a central rod at the axis and a plurality of uniformly spaced planar discs coaxial to the rod and to each other, the plane of said discs being perpendicular to the central rod.

31. The solid phase matrix of claim 25 wherein the number of said fin-like projections ranges from 8 to 18.

32. The solid phase matrix of claim 25 wherein the number of said fin-like projections ranges from 16 to 18.

33. The solid phase matrix of claim 24 fabricated by a molding process using a mold with polished surfaces.

34. The solid phase matrix of claim 24 wherein the elements attached to the handle member are so dimensioned as to render the same size matrix suitable for use in reaction fluid volumes varying by at least 3-fold.

35. A solid phase matrix for insertion into a reaction vessel containing a fluid sample to be assayed for the presence of a given mobile component, which matrix comprises (1) a handle member having affixed thereto at one end a plurality of elements having essentially smooth plane or curved surfaces so arranged with respect to one another and the handle member, and of a size and shape such that the average diffusion distance between mobile component molecules and solid surface is greatly reduced relative to the average diffusion distance between mobile component molecules and the walls of the reaction vessel when no solid matrix is present; (2) wherein each of said elements is substantially uniformly coated with a composition comprising a fixed component to which the mobile component being assayed for, if present, will adhere, the amount of said fixed component being so selected that adherence of the mobile component will occur at a rate measurable as a function of total concentration of mobile component in the fluid sample; and (3) wherein the number, placement, size and shape of said elements is correlated with the amount of fixed component and the other physical and chemical characteristics of the coating composition to insure maximum availability of active fixed component at the surfaces of the elements.

36. The solid phase matrix of claim 35 comprising a central rod and a plurality of fin-like projections extending outwardly from said rod along a portion of the length of said rod.

37. The solid phase matrix of claim 35 wherein the number of said fin-like projections ranges from 8 to 18.

38. The solid phase matrix of claim 35 wherein the number of said fin-like projections ranges from 16 to 18.

39. The solid phase matrix of claim 35 fabricated by a molding process using a mold with polished surfaces.

40. The solid phase matrix of claim 35 wherein the elements attached to the handle member are so dimensioned as to render the same size matrix suitable for use in reaction fluid volumes varying by at least 3-fold.

* * * * *

UNITED STATES PATENT OFFICE
CERTIFICATE OF CORRECTION

Patent No. 4,225,575                  Dated Sep. 30, 1980

Inventor(s) Roger N. Piasio et al

It is certified that error appears in the above-identified patent and that said Letters Patent are hereby corrected as shown below:

| | |
|---|---|
| Col. 4, l. 34 | "reactants" should be -- reagent-- |
| Col. 19, l. 2 | "phosphte" should be --phosphate-- |
| Col. 20, l. 56 | "process" should be --presence-- |
| Col. 21, l. 10 | "while" should be --While-- |

Signed and Sealed this

Twenty-seventh Day of January 1981

[SEAL]

Attest:

RENE D. TEGTMEYER

Attesting Officer        Acting Commissioner of Patents and Trademarks